United States Patent
Qu et al.

(10) Patent No.: US 7,339,063 B2
(45) Date of Patent: Mar. 4, 2008

(54) QUINOLYL ORGANIC GERMANIUM ESTER AND THE SYNTHESIS METHOD THEREOF

(75) Inventors: Xiaogang Qu, Changchun (CN); Guoqiang Shangguan, Changchun (CN)

(73) Assignee: Changchun Institute of Applied Chemistry Chinese Academy of Sciences, Changchun (CN)

( * ) Notice: Subject to any disclaimer, the term of this patent is extended or adjusted under 35 U.S.C. 154(b) by 478 days.

(21) Appl. No.: 11/148,738

(22) Filed: Jun. 9, 2005

(65) Prior Publication Data

US 2005/0282795 A1    Dec. 22, 2005

(30) Foreign Application Priority Data

Jun. 16, 2004   (CN) .......................... 2004 1 0010925

(51) Int. Cl.
  *C07D 215/12* (2006.01)
(52) U.S. Cl. ............................................ 546/174; 546/2
(58) Field of Classification Search ................ 546/174, 546/2
  See application file for complete search history.

(56) References Cited

FOREIGN PATENT DOCUMENTS

CN            1629166 A   *   6/2005

\* cited by examiner

*Primary Examiner*—D. Margaret Seaman
(74) *Attorney, Agent, or Firm*—Kinney & Lange, PA

(57) ABSTRACT

The present invention relates to compounds of quinolyl organic germanium ester having the following Formula 1 and the synthesis methods thereof. $R_1$ and $R_2$ are defined in the specification. Organic germanium acyl chloride and 8-hydroxylquinoline were used as the starting raw materials. Displacement reaction was carried out at 0-40° C., followed by hydrolysis reaction and then by changing the solvent, water soluble quinolyl organic germanium ester was finally obtained. The quinolyl organic germanium ester possesses better water solubility and fat solubility. Due to the existence of both drug active group (organic germanium part) and drug recognizing group (quinoline part) in the structure of the quinolyl organic germanium ester, the compound is expected to develop a novel kind of anti-tumor drug (I)

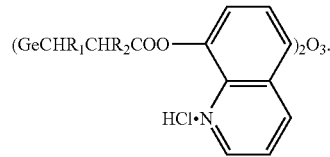

3 Claims, 1 Drawing Sheet

QUINOLYL ORGANIC GERMANIUM ESTER AND THE SYNTHESIS METHOD THEREOF

FIELD OF THE INVENTION

The present invention relates to the compounds of quinolyl organic germanium ester and the synthesis methods thereof.

BACKGROUND OF THE INVENTION

Since Dr. Kazuhiko Asai et al in Japan successfully synthesized bis-β-carboxyethyl germanium sesquioxide: $(GeCH_2CH_2COOH)_2O_3$, i.e. Ge-132, and found it to possess biological effects of anti-tumor, anti-virus, anti-senium, researches on synthesis of novel organic germanium compound and anti-tumor activity became important fields to develop high efficient and low toxic anti-tumor drugs. Scientists have successfully synthesized many kinds of organic germanium compounds such as derivatives of Ge-132, analogs containing —$GeO_3$ group, endoxy germanium ring type compounds and the like and studied their anti-tumor effects in many respects. Since seventieth last century, scientists in Japan, United States of America, China and former USSR successively synthesized about one thousand organic germanium compounds and studied their anti-tumor activities in many respects. More than 800 papers and authorized patents were published. Most researches performed in China or abroad related only to chemical synthesis of organic germanium compounds or to their activity screening. However, the correlation of organic groups was not emphasized, influence of molecule as a whole on the anti-tumor effect was neglected, and research on recognition selectivity of compound towards tumor cells and DNA was not touched. As a result, active compounds having strong anti-tumor activity, high selective recognizability, high researchable value and potential applications have not yet been obtained.

DESCRIPTION OF THE INVENTION

The objective of the present invention is to provide a quinolyl organic germanium ester compound.

Another objective of the present invention is to provide a method for preparation of quinolyl organic germanium ester compound.

In the present invention, organic germanium compounds with novel structure were synthesized through molecular design that retains the basic structure of organic germanium sesquioxide while introduces quinolyl groups capable of having interaction with DNA and having pharmaceutical activity itself and spectroscopic properties into the molecule. Due to the existence of synergic effect, the new compounds not only possess relatively strong anti-tumor activity and better selective recognizability but also promote researches on their anti-tumor mechanism such as research on the interaction and recognition between the said novel compound and in vivo bio-macromolecules through spectroscopic methods. This will provide new idea, product and technical method for deeper research of organic germanium drug.

The present invention provides a quinolyl organic germanium ester compound having the following structure (Formula I):

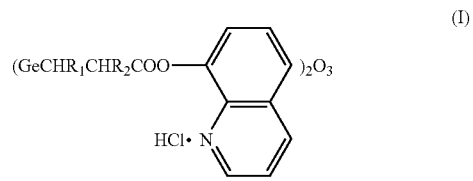

where $R_1$ and $R_2$ are independently selected from the group consisted of H, alkyl having 1-6 carbon atoms or —$C_6H_5$.

Preferably, $R_1$ and $R_2$ are independently selected from the group consisted of H, —$CH_3$ or —$C_6H_5$.

The present invention also relates to a method for synthesizing the quinolyl organic germanium ester compounds, comprising:

(1) adding 8-Hydroxyl-quinoline and organic germanium acyl chloride to dichloromethane at 0-40° C., reacting for 2-6 hrs to obtain a yellow precipitate, wherein the mole ratio of the 8-Hydroxyl-quinoline and organic germanium acyl chloride is in a range of 0.2-0.4:0.05-0.1;

(2) filtering off the precipitate and evaporating filtrate to obtain a pale yellow viscous liquid, washing, and freezing the washing solution to precipitate yellow solid;

(3) collecting the yellow solid, dissolving in water, transferring the aqueous solution to acetone at 0-30° C., stirring and filtering to collect a precipitate, and obtaining the quinolyl organic germanium ester compound.

The synthetic reaction involved in the present invention is as follows:

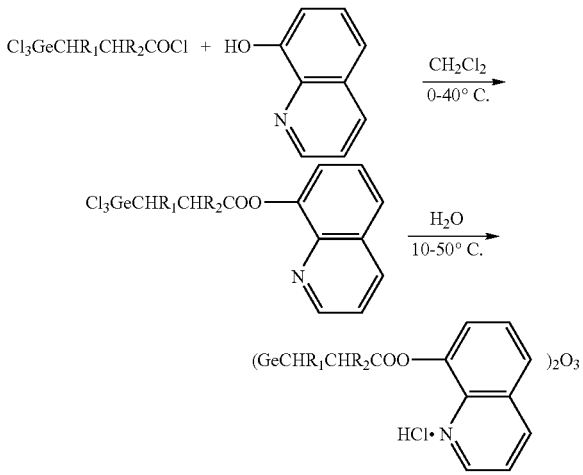

The specific synthetic steps involved are as follows:

(1) To the dichloromethane solvent at 0-40° C., 8-hydroxyl-quinoline and organic germanium propionyl chloride are successively added. The mole ratio of the 8-Hydroxyl-quinoline and organic germanium acyl chloride is in a range of 0.2-0.4:0.05-0.1. The mixture is thoroughly stirred and allowed to react for 2-6 hr. A yellow precipitate is obtained.

(2) The precipitate is filtered off and the filtrate is rotary-evaporated to give a yellow viscous liquid which is washed with tetrahydrofuran. Yellow solid is separated out from the washed solution by freezing.

(3) The yellow solid is collected and small amount of water is added to it within 1-10 minutes to form an aqueous solution which was transferred to acetone at 0-30° C. Then the solution was stirred for 10-40 min and the precipitate was collected by filtration, followed by washed successively with cold water, ethanol, and acetone. The final product of quinolyl organic germanium ester compound was obtained with yield of 30-75%.

Figure 1:
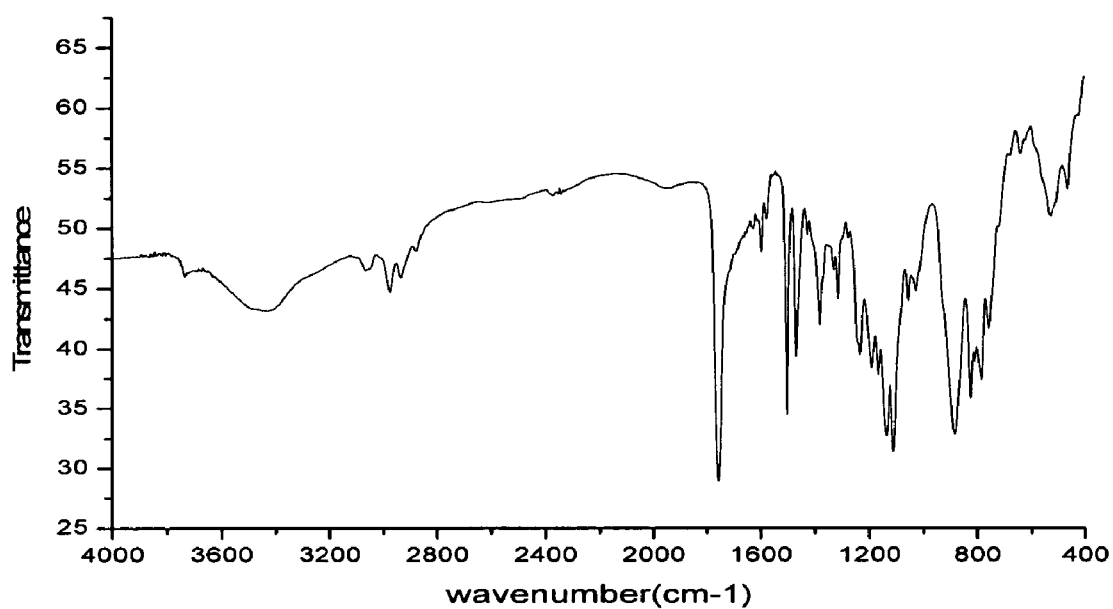
FIG. 1 is infrared spectrum of quinolyl organic germanium ester compound.

In the infrared spectrum of the said product, it exhibits a strong absorption peak of ester bond at 1760 cm$^{-1}$, a strong characteristic peak of Ge—O bond at 800-900 cm$^{-1}$ and a median strong peak of Ge—C bond at 528 cm$^{-1}$.

The organic germanium compounds synthesized in the present invention not only retains the basic structure of organic germanium sesquioxide but also introduces chromophore group of quinoline into the molecule. They possess better water solubility, fat solubility and higher heat stability and would not decompose in air during long time storage. It is confirmed in Experiments that the compounds possess relatively high anti-tumor activity, extremely strong UV absorption and fluorescence property which provides the necessary condition for investigation of their anti-tumor property and mechanism of action and provides meaningful data for further designing of synthesizing novel organic germanium anti-tumor drugs and for research of anti-tumor mechanism of action at molecular level.

EXAMPLE 1

Synthesis of Quinolyl Germanyl Propionate Sesquioxide

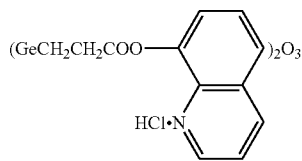

Trichlorogermyl propionyl chloride was synthesized according to method reported in literature.

Under cooling of ice-bath, a solution of 0.025 mol of trichlorogermyl propionyl chloride in 20 ml of Dichloromethane was added dropwise into a solution of 0.05 mol of 8-hydroxyl-quinoline in 40 ml of dichloromethane with stirring. The mixture was stirred and allowed to react for 5 hrs and was rotary-evaporated to remove the solvent. Then residue was washed with 20 ml tetrahydrofuran and the yellow solid was separated out of the washed solution by freezing. The yellow solid was collected and thoroughly washed with cold tetrahydrofuran.

The solid was dissolved in 5 ml of water. After 3 min, the aqueous solution was transferred to 50 ml of acetone at 0-5° C. and stirred for 10 min. The precipitate was collected by filtration and was washed successively with cold water, ethanol and cold acetone and dried in vacuum. The product thus obtained contains 2 molecules of water of crystallization and the final yield was 69%.

Structure characterization of the product: (1) Infrared spectrum: a strong absorption peak of ester bond at about 1757 cm$^{-1}$, a strong characteristic peak of Ge—O bond at 883 cm$^{-1}$ and a median strong peak of Ge—C bond at 525 cm$^{-1}$. (2) NMR: chemical shift δ=1.68: 2H, triple peak, —CH$_2$; δ=2.82: 2H, triple peak, —CH$_2$; δ=7-8.0: 6H, multiple peak, quinoline hydrogen. (3) Elementary analysis $C_{24}H_{22}N_2O_7Ge_2Cl_2 \cdot 2H_2O$: Found %: C, 40.62; H, 3.77; N, 3.92; Ge, 20.57. Calcd for %: C, 41.01; H, 3.70; N, 3.99; Ge, 20.68.

EXAMPLE 2

Synthesis of Quinolyl Germanyl-α-methyl Propionate Sesquioxide

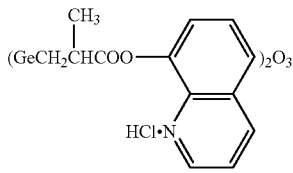

In the synthesis of trichlorogermanyl-α-methyl propionyl chloride, acrylic acid was replaced by α-methyl acrylic acid.

Experimental method and conditions were similar to those of Example 1. The difference was that Trichlorogermyl propionyl chloride was replaced by trichlorogermanyl-α-methyl propionyl chloride; When hydrolyzed solution was transferred to acetone, pale yellow sticky solid began to appear which would be solidified by continued stirring. The obtained product contains 1 molecule of water of crystallization. The yield was 30%.

Structure characterization of the product: (1) Infrared spectrum: as illustrated in the attached figure, a strong absorption peak of ester bond at about 1760 cm$^{-1}$, a strong characteristic peak of Ge—O bond at 800-900 cm$^{-1}$ and a median strong peak of Ge—C bond at 528 cm$^{-1}$. (2) NMR: chemical shift δ=1.53: 3H, multiple peak, —CH$_3$; δ=2.75: 2H, triple peak, —CH$_2$; δ=3.0-3.6: 1H, multiple peak, —CH; δ=7.0-8.0: 6H, multiple peak, quinoline hydrogen. (3) Elementary analysis $C_{26}H_{26}N_2O_7Ge_2Cl_2 \cdot H_2O$: Found %: C, 44.22; H, 4.21; N, 3.89; Ge, 19.72. Calcd for %. C, 42.47; H, 4.11; N, 3.84; Ge, 19.88

EXAMPLE 3

Synthesis of Quinolyl Germanyl-β-methyl Propionate Sesquioxide

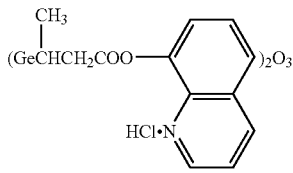

In the synthesis of trichlorogermanyl-β-methyl propionyl chloride, acrylic acid was replaced by β-methacrylic acid.

Experimental method and conditions were similar to those of Example 2. The difference was that trichlorogermyl-α-propionyl chloride was replaced by trichlorogermanyl-β-methyl propionyl chloride; Obtained product contains 1 molecule of water of crystallization. The yield was 62%.

Structure characterization of the product: (1) Infrared spectrum: a strong absorption peak of ester bond at about 1755 cm$^{-1}$, a strong characteristic peak of Ge—O bond at 883 cm$^{-1}$ and a median strong peak of Ge—C bond at 525 cm$^{-1}$. (2) NMR: chemical shift δ=1.51: 3H, multiple peak, —CH$_3$; δ=2.72: 2H, triple peak, —CH$_2$; δ=3.2-3.7: 1H, multiple peak, —CH; δ=7.2-8.0: 6H, multiple peak, quinoline hydrogen. (3) Elementary analysis $C_{26}H_{26}N_2O_7Ge_2Cl_2 \cdot H_2O$: Found %: C, 42.16; H, 4.23; N, 3.78; Ge, 19.76. Calcd for %: C, 42.47; H, 4.11; N, 3.84; Ge, 19.88.

EXAMPLE 4

Synthesis of Quinolyl Germanyl-β-phenyl Propionate Sesquioxide

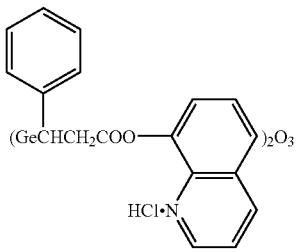

In the synthesis of trichlorogermanyl-β-phenyl propionyl chloride, acrylic acid was replaced by β-phenyl acrylic acid.

Experimental method and conditions were similar to those of Example 2. The difference was that trichlorogermyl-α-methyl propionyl chloride was replaced by trichlorogermanyl-β-phenyl propionyl chloride. The obtained product contains 1 molecule of water of crystallization. The yield was 46%.

Structure characterization of the product: (1) Infrared spectrum: a strong absorption peak of ester bond at about 1760 cm$^{-1}$, a strong characteristic peak of Ge—O bond at 885 cm$^{-1}$ and a median strong peak of Ge—C bond at 533 cm$^{-1}$. (2) NMR: chemical shift δ=2.75: 2H, triple peak, —CH$_2$; δ=3.4-3.9: 1H, multiple peak, —CH; δ=7.2-7.5: 5H, multiple peak, benzene ring hydrogen; 7.7-8.2: 6H, multiple peak, quinoline hydrogen. (3) Elementary analysis $C_{36}H_{30}N_2O_7Ge_2Cl_2.H_2O$: Found %: C, 51.73; H, 3.95; N, 3.31; Ge, 17.42. Calcd for %; C,51.66; H, 3.83; N, 3.35; Ge, 17.36.

EXAMPLE 5

Synthesis of Quinolyl Germanyl Propionate Sesquioxide

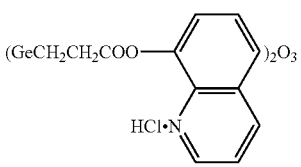

The raw materials and reagents used were identical with those of Example 1 except for variation of mole ratio of reactants and the experimental conditions.

At room temperature, a solution of 0.025 mol of trichlorogermyl propionyl chloride in 20 ml of Dichloromethane was added dropwise into a solution of 0.1 mol of 8-hydroxyl-quinoline in 60 ml of dichloromethane with stirring. The mixture was stirred and allowed to react for 6 hrs and was rotary-evaporated to remove the solvent. Then residue was washed with 30 ml tetrahydrofuran and the yellow solid was separated out of the washed solution by freezing. The yellow solid was collected and thoroughly washed with cold tetrahydrofuran.

The solid was dissolved in 5 ml of water. After 5 min, the aqueous solution was transferred to 50 ml of acetone at 10-15° C. and stirred for 20 min. The precipitate was collected by filtration and was washed successively with cold water, ethanol and cold acetone and dried in vacuum. The product thus obtained contains 2 molecules of water of crystallization and the final yield was 75%.

Infrared spectrum and NMR profile are identical with those of Example 1 and the result of elementary analysis agrees with $C_{24}H_{22}N_2O_7Ge_2Cl_2.2H_2O$.

EXAMPLE 6

Synthesis of Quinolyl Germanyl-α-methyl Propionate Sesquioxide

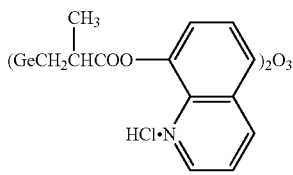

The experimental method and conditions were identical with those of Example 5. The difference was that trichlorogermanyl propionyl chloride was replaced by trichlorogermanyl-α-methyl propionyl chloride. After the hydrolyzed liquid was transferred to acetone, yellow sticky solid began to appear which was solidified by continued stirring. The obtained product contains 1 molecule of water of crystallization. The yield was 53%.

Infrared spectrum and NMR profile were identical with those of Example 2 and the result of elementary analysis agrees with $C_{26}H_{26}N_2O_7Ge_2Cl_2.H_2O$.

EXAMPLE 7

Synthesis of Quinolyl Germanyl-β-methyl Propionate Sesquioxide

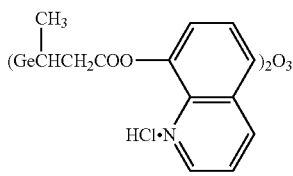

The experimental method and conditions were identical with those of Example 6. The difference was that trichlorogermanyl-α-methyl propionyl chloride was replaced by trichlorogermanyl-β-methyl propionyl chloride. The obtained product contains 1 molecule of water of crystallization. The yield was 71%.

Infrared spectrum and NMR profile were identical with those of Example 3 and the result of elementary analysis agrees with $C_{26}H_{26}N_2O_7Ge_2Cl_2.H_2O$.

EXAMPLE 8

Synthesis of Quinolyl Germanyl-β-phenyl Propionate Sesquioxide

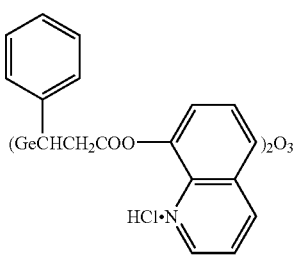

In the synthesis of trichlorogermanyl-β-phenyl propionyl chloride, acrylic acid was replaced by β-phenyl acrylic acid.

Experimental method and conditions are similar to those of Example 6. The difference lies on that trichlorogermanyl-α-methyl propionyl chloride was replaced by trichlorogermanyl-β-phenyl propionyl chloride; The product obtained contains 1 molecule of water of crystallization. The yield was 58%.

Infrared spectrum and NMR profile were identical with those of Example 4 and the result of elementary analysis agrees with $C_{36}H_{30}N_2O_7Ge_2Cl_2 \cdot H_2O$.

EXAMPLE 9

Cytotoxicity of Quinolyl Germanyl Propionate Sesquioxide (a) and Quinolyl Germanyl-α-methyl Propionate Sesquioxide (b) Against PC-3M Prostate Cancer Cell Line Table 1 summarizes the inhibition effects of the two compounds on the PC-3M proliferation. The inhibition is not only concentration and time dependent, but also methyl substitution related. The only difference of these two compounds is with or without the methyl group in the linking chain of the Germanium and quinoline. Without the methyl group, Compound (a) has stronger inhibition effect than Compound (b). The $IC_{50}$ of Compound (a) which was measured by MTT method was 10 μM, three fold lower than that of Compound (b).

TABLE 1

Summary of the inhibition effect of the two compounds on PC-3M proliferation

| Concentration (μM)* | 24 h | | 48 h | | 72 h | |
|---|---|---|---|---|---|---|
| | a | b | a | b | a | b |
| 10 | 0.34** | 0.09 | 0.69 | 0.32 | 0.62 | 0.58 |
| 30 | 0.48 | 0.30 | 0.74 | 0.45 | 0.74 | 0.69 |
| 60 | 0.50 | 0.20 | 0.74 | 0.43 | 0.78 | 0.67 |

*The compound concentration we used;
**the inhibition fraction at the given concentration.

What is claimed is:

1. A quinolyl organic germanium ester compounds having the following structure (I):

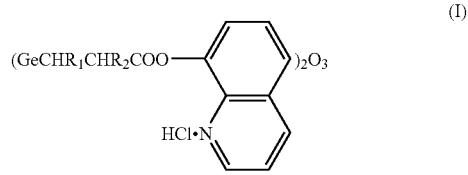

where $R_1$ and $R_2$ are independently selected from the group consisted of H, alkyl having 1-6 carbon atoms or —$C_6H_5$.

2. The compound according to claim 1, wherein the $R_1$ and $R_2$ are independently selected from the group consisted of H, —$CH_3$ or —$C_6H_5$.

3. A method for synthesizing the quinolyl organic germanium ester compounds according to claim 1, comprising:
   (1) adding 8-Hydroxyl-quinoline and organic germanium acyl chloride to dichloromethane at 0-40° C., reacting for 2-6 hrs to obtain a yellow precipitate, wherein the mole ratio of the 8-Hydroxyl-quinoline and organic germanium acyl chloride is in a range of 0.2-0.4:0.05-0.1;
   (2) filtering off the precipitate and evaporating filtrate to obtain a pale yellow viscous liquid, washing, and freezing the washing solution to precipitating yellow solid;
   (3) collecting the yellow solid, dissolving in water, transferring the aqueous solution to acetone at 0-30° C., stirring and filtering to collect a precipitate, and obtaining the quinolyl organic germanium ester compound.

* * * * *